US010292725B2

United States Patent
Hart et al.

(10) Patent No.: US 10,292,725 B2
(45) Date of Patent: May 21, 2019

(54) INCISION-LESS LAPAROSCOPIC INSTRUMENT

(71) Applicants: Stuart Hart, Tampa, FL (US); Susana Lai-Yuen, Tampa, FL (US); Erin Moree, Tampa, FL (US); James Doulgeris, Oldsmar, FL (US); Benjamin Taylor Nelson, Tampa, FL (US); Grahm Roach, San Antonio, TX (US); Brandon Kruse, Tampa, FL (US)

(72) Inventors: Stuart Hart, Tampa, FL (US); Susana Lai-Yuen, Tampa, FL (US); Erin Moree, Tampa, FL (US); James Doulgeris, Oldsmar, FL (US); Benjamin Taylor Nelson, Tampa, FL (US); Grahm Roach, San Antonio, TX (US); Brandon Kruse, Tampa, FL (US)

(73) Assignee: University of South Florida, Tampa, FL (US)

( * ) Notice: Subject to any disclaimer, the term of this patent is extended or adjusted under 35 U.S.C. 154(b) by 369 days.

(21) Appl. No.: 15/200,730

(22) Filed: Jul. 1, 2016

(65) Prior Publication Data

US 2016/0310160 A1  Oct. 27, 2016

Related U.S. Application Data

(63) Continuation of application No. 13/693,252, filed on Dec. 4, 2012, now Pat. No. 9,381,029, which is a
(Continued)

(51) Int. Cl.
*A61B 17/32* (2006.01)
*A61B 17/29* (2006.01)
(Continued)

(52) U.S. Cl.
CPC ...... *A61B 17/320016* (2013.01); *A61B 17/29* (2013.01); *A61B 17/32* (2013.01);
(Continued)

(58) Field of Classification Search
CPC ........ A61B 17/320016; A61B 17/3201; A61B 17/32; A61B 17/29; A61B 17/3417;
(Continued)

(56) References Cited

U.S. PATENT DOCUMENTS 5,322,055 A  6/1994  Davison et al.
6,007,561 A  12/1999  Bourque et al.
(Continued)

OTHER PUBLICATIONS

Aurora D. Pryor, John R. Tushar, Louis R. DiBernardo, Single-port cholecystectomy with the TransEnterix SPIDER: simple and safe, Surg Endosc (2010) 24:917-923.
(Continued)

*Primary Examiner* — Richard G Louis
(74) *Attorney, Agent, or Firm* — Andriy Lytvyn; Smith & Hopen, P.A.

(57) ABSTRACT

A laparoscopic instrument is placed into the abdomen without the creation of a skin incision. The laparoscopic instrument includes a shaft that does not exceed 1.6 mm in diameter. The shaft has a beveled end and is inserted into an abdomen similar to the placement of a needle, without use of a scalpel. Operating instruments are introduced into the abdomen through the umbilical port using a docking device, and are then docked to the beveled end of the shaft after the shaft is introduced through the abdomen. Multiple types of operating instruments can be placed on the beveled end of the shaft during the surgical procedure. Each operating instrument is docked with a holster during introduction into and withdrawal from the umbilical port and is removed from
(Continued)

the holster only when in use. When removed from the holster it is locked to the shaft and cannot be dropped.

17 Claims, 11 Drawing Sheets

Related U.S. Application Data continuation of application No. PCT/US2011/039272, filed on Jun. 6, 2011.

(60) Provisional application No. 61/351,512, filed on Jun. 4, 2010.

(51) Int. Cl.
    *A61B 17/34*     (2006.01)
    *A61B 17/3201*     (2006.01)
    *A61B 17/00*     (2006.01)

(52) U.S. Cl.
CPC ...... *A61B 17/3201* (2013.01); *A61B 17/3417* (2013.01); *A61B 2017/00345* (2013.01); *A61B 2017/00353* (2013.01); *A61B 2017/00362* (2013.01); *A61B 2017/00464* (2013.01); *A61B 2017/00473* (2013.01); *A61B 2017/00477* (2013.01); *A61B 2017/2931* (2013.01); *A61B 2017/3456* (2013.01)

(58) Field of Classification Search
CPC .. A61B 2017/00362; A61B 2017/3456; A61B 2017/2931; A61B 2017/00473; A61B 2017/00464; A61B 2017/00353; A61B 2017/00345; A61B 2017/00477
See application file for complete search history.

(56) References Cited

U.S. PATENT DOCUMENTS

| 2004/0138701 A1 | 7/2004 | Haluck |
| 2008/0215051 A1 | 9/2008 | Buysse et al. |
| 2009/0012477 A1 | 1/2009 | Norton et al. |

OTHER PUBLICATIONS

International Preliminary Report on Patentability for International Application No. PCT/US2011/039272, dated Feb. 17, 2012.
International Search Report for International Application No. PCT/US2011/039272, dated Feb. 17, 2012.
Aziz M. Merchant & Michael W. Cook & Brent C. White & S. Scott Davis & John F. Sweeney & Edward Lin, Transumbilical Gelport Access Technique for Performing Single Incision Laparoscopic Surgery (SILS), J Gastrointest Burg (2009) 13:159-162.
Athanassios C. Petrotos, Bruce M. Molinelli, Single-incision multiport laparoendoscopic (SIMPLE) surgery: early evaluation of SIMPLE cholecystectomy in a community setting, Surg Endosc (2009) 23:2631-2634.
Alan A. Saber & Mohamed H. Elgamal & Ed A. Itawi & Arun J. Rao, Single Incision Laparoscopic Sleeve Gastrectomy (SILS): A Novel Technique, Obes Surg, 2008, pp. 1-5.

INCISION-LESS LAPAROSCOPIC INSTRUMENT

CROSS REFERENCE TO RELATED APPLICATIONS

This application is a continuation of U.S. Nonprovisional application Ser. No. 13/693,252, entitled, "Incision-Less Laparoscopic Instrument", filed Dec. 4, 2012, which claims priority to International Patent Application No. PCT/US2011/039272, entitled "Incision-Less Laparoscopic Instrument", filed on Jun. 6, 2011 which is a non-provisional of and claims priority to U.S. Provisional Appl. No. 61/351,512, entitled, "Incision-Less Laparoscopic Instrument", filed Jun. 4, 2010, the contents of which are herein incorporated by reference.

BACKGROUND OF THE INVENTION

1. Field of the Invention

This invention relates to the field of laparoscopic surgical devices.

2. Description of the Prior Art

Laparoscopic (minimally invasive) surgery has become the standard for performing numerous surgical procedures across various surgical specialties. Traditionally, an incision is made in the umbilicus for insertion of a port containing a camera device for visualization during laparoscopic surgery. Placement of laparoscopic instruments during laparoscopic surgery requires the creation of multiple skin incisions with a scalpel, and then placement of laparoscopic ports. Multiple laparoscopic instruments can then be passed through each laparoscopic port to perform the surgical procedure. Typically, laparoscopic ports range from five (5) to twelve millimeters (12 mm) in diameter, and leave an abdominal scar and contribute to post-operative pain. Usually, three to four laparoscopic ports are placed during traditional laparoscopic surgery.

Laparo-Endoscopic Single Site (LESS) surgery has been introduced as a means to perform minimally invasive surgery without noticeable abdominal incisions, and to improve post-operative pain. LESS surgery is performed entirely through a single incision in the umbilicus. This eliminates multiple incisions during laparoscopic surgery, but also creates many challenges. Since the surgery is performed entirely through a single umbilical incision, and the instruments are in close proximity to each other, the ability to manipulate instruments during the surgery is limited. This creates "sword fighting," in which the instruments constantly collide into each other during surgery, and contributes to inefficient surgical movements. There is also loss of triangulation, in which instruments are traditionally inserted into the abdomen at multiple different port sites and allows for easy manipulation of tissue since the angles of the instruments are varied. These challenges ultimately increase surgical operative time and reduce efficiency of the surgery.

Thus there is a need for a system that avoids instrument collision while still providing robust surgical devices. However, in view of the prior art considered as a whole at the time the present invention was made, it was not obvious to those of ordinary skill in the applicable art how such a system could be provided.

SUMMARY OF INVENTION

The novel laparoscopic instrument can be placed into an abdomen without the creation of a skin incision. The shaft of the laparoscopic instrument is 1.6 mm in diameter with a beveled end, resembling an intravenous needle. The beveled end is placed into the abdomen similar to the placement of a needle, without creation of a skin incision with a scalpel.

The operating instruments, such as graspers, cutting forceps or cautery instruments, are docked to the beveled end of the shaft after the shaft is placed into the abdomen. These operative instruments are introduced into the abdomen through the umbilical port using a docking device, and then docked to the beveled end of the shaft. When docking is completed, the docking device is removed and the surgical procedure is performed. Multiple types of instrument tips can be placed on the beveled end of the shaft during the surgical procedure using the docking device to engage and disengage the surgical instruments. At the end of the surgical procedure, the operative instruments are undocked and the 1.6 mm shaft is removed. This allows the surgeon to place multiple instruments, in any location, during the laparoscopic surgery, thus preserving triangulation and efficiency of the surgery without creating abdominal scars.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

The present invention relates to a laparoscopic instrument that is placed into the abdomen at any preselected location without the creation of a skin incision. The shaft of the laparoscopic instrument is 1.6 mm in diameter with a beveled end that resembles an intravenous needle.

Selected operating instruments, such as graspers, cutting forceps or cautery instruments, having diameters that exceed 1.6 mm, are introduced into the abdomen through the umbilical port. The selected operating instrument is docked in a holster when it is introduced through said umbilical port. This prevents unwanted cutting or grasping of tissue, i.e., the operating instrument cannot be used until it is removed from the holster.

A novel locking or docking mechanism is positioned at the trailing end of the selected operating instrument and is engaged by the leading end of the laparoscopic instrument shaft. That shaft is hereinafter referred to as the outer shaft because it houses an inner shaft within its lumen and said inner shaft controls the opening and closing of the blades or graspers at the leading end of the selected operating instrument.

A predetermined surgical procedure is performed after the selected operating instrument is removed from the holster and said selected operating instrument is returned to the holster and locked therein when the surgical procedure is completed. The laparoscopic instrument is then disengaged from the locking mechanism and withdrawn from the abdomen. The selected operating instrument and its holster are withdrawn through said umbilical port.

Multiple types of instrument tips can be placed on the beveled end of the outer shaft during the surgical procedure using the docking device or locking mechanism to "dock" and "undock" the operating instruments. This allows the surgeon to place multiple instruments in any location during the laparoscopic surgery, thus preserving triangulation and efficiency of the surgery without creating abdominal scars.

Figure 1:
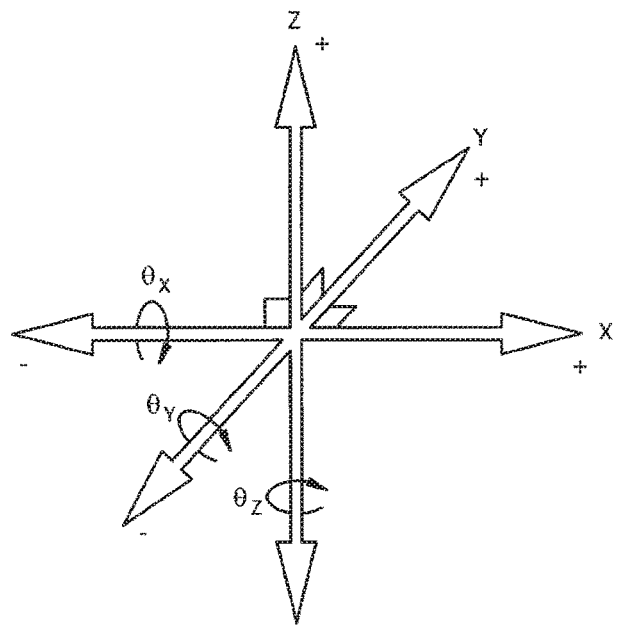
FIG. 1 depicts the six degrees of freedom of an unrestrained body.

To prevent an object from moving relative to another object, all degrees of freedom of motion must be constrained. An object with no constraints has six degrees of freedom (DOF) as depicted in FIG. 1: Translation along the X, Y, and Z axis, and rotation about the X, Y, and Z axis. Thus, for the operative instrument tip, all six of these DOF need to be constrained in order to lock the operative instrument tip onto the shaft.

The selected operating instrument locks onto the instrument outer shaft, restricting its movement on said outer shaft. It is impossible to drop the selected operating instrument because the docking and undocking of the selected operating instrument with the holster is performed by the same locking mechanism.

Figure 2:
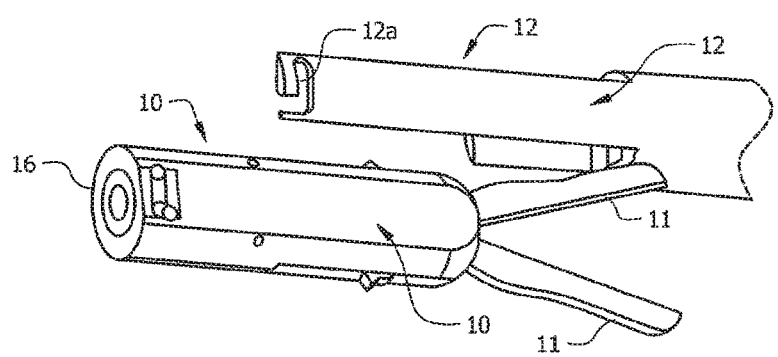
FIG. 2 is an exploded perspective view of an operative instrument tip and holster.

When operative instrument tip 10 having blades 11, also known as scissors or graspers, is docked inside holster 12 (FIG. 2), face pin depression pins 14 (FIG. 4) extend through operative instrument tip 10 to locking mechanism 16 at the trailing end of said operative instrument tip. Face pin depression pins 14 depress face pin 18 (FIG. 3) causing face pin 18 to be flush with inner lock ring 20. Face pin 18, when flush with inner lock ring 20, does not obstruct rotation of inner lock ring 20.

Operative instrument tip 10 is hereinafter referred to as cutting head 10.

Figure 3A:
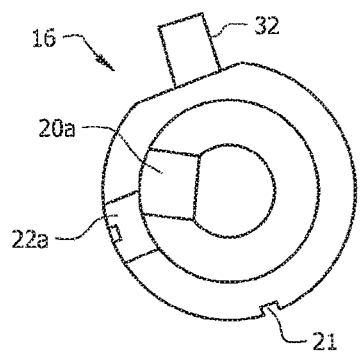
FIG. 3A is a front elevational view of a locking mechanism.
Figure 3B:
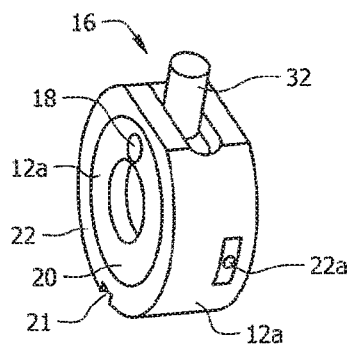
FIG. 3B is a perspective view of the locking mechanism of FIG. 3A.
Figure 4:
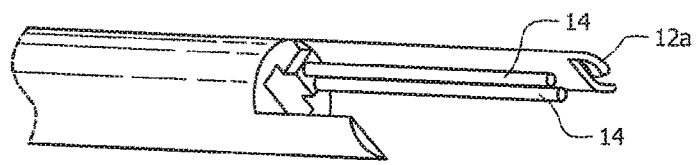
FIG. 4 is a perspective view of a holster key.

Inner lock ring 20 is circumscribed by outer lock ring 22 as depicted in FIGS. 3A and 3B. Keyway 22b formed in the outer periphery of outer lock ring 22 interlocks said outer lock ring to the housing of cutting head 10.

Figure 6A:
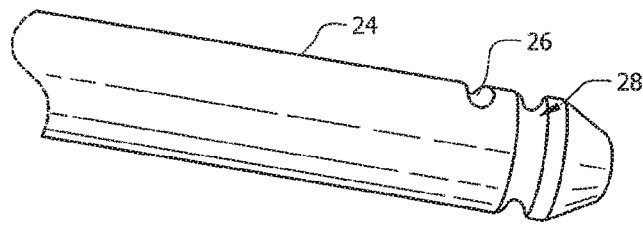
FIG. 6A is a perspective view of the outer shaft.
Figure 6B:
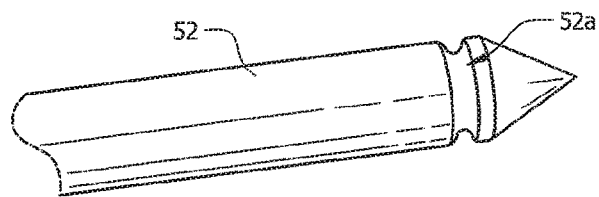
FIG. 6B is a perspective view of the inner shaft.

Outer shaft 24 (FIG. 6A) is inserted into locking mechanism 16 so that inner lock ring pin 20a (FIG. 3A) rests in lock groove 26 (FIG. 6) of outer shaft 24, and an O-ring, not depicted, associated with inner lock ring 20 is received within O-ring groove 28 (also FIG. 6A).

Inner shaft 52 (FIG. 6B) controls opening and closing of blades or graspers 11. Distal-to-proximal displacement of inner shaft 52 opens said blades or graspers and proximal-to-distal displacement closes them. The opposite effect can also be achieved by suitable mechanical linkages and all known linkages are within the scope of this invention.

Inner lock ring pin 20a and outer lock ring pin 22a of outer lock ring 22 are pushed into a position by outer shaft 24 that radially aligns them with one another. Lock ring pins 20a and 22a in said radially aligned position allow inner lock ring 20 to rotate inside outer lock ring 22 and keep outer shaft 24 from sliding in and out.

Figure 5:
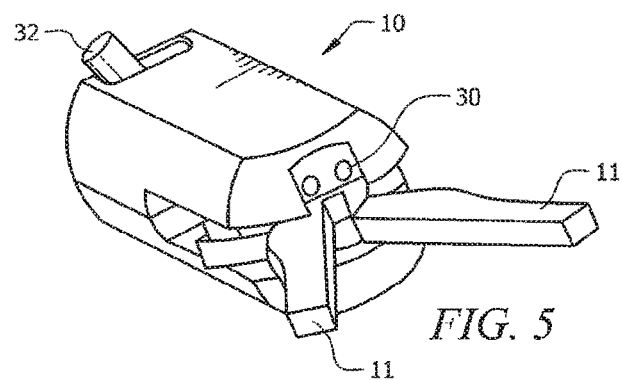
FIG. 5 is a perspective view of an operative instrument tip or cutting head.

By rotating outer shaft 24, inner lock ring 20 can rotate fully into position. This causes face pin 18 to align with face pin holes 30 (FIG. 5) and causes holster lock pin 32 to move into a position that is unlocked from holster 12. This is the retracted position of face pin 18. Outer shaft 24 is now locked onto cutting head 10 and can be removed from holster 12. Face pin 18 snaps back into place, i.e., into an extended configuration, when cutting head 10 is slightly removed from holster 12. When extended, face pin 18 prevents inner lock ring 20 from rotating inside cutting head 10.

Cutting head 10 is slid back onto holster 12 and outer shaft 24 is rotated fully in the counterclockwise direction to lock cutting head 10 back onto holster 12 and align lock ring pins 20a and 22a in radial alignment with one another when the surgical procedure is completed. Outer shaft 24 can be removed from cutting head 10 when lock ring pins 20a and 22a are radially aligned with one another.

A more detailed explanation of the above structure follows.

Figure 7A:
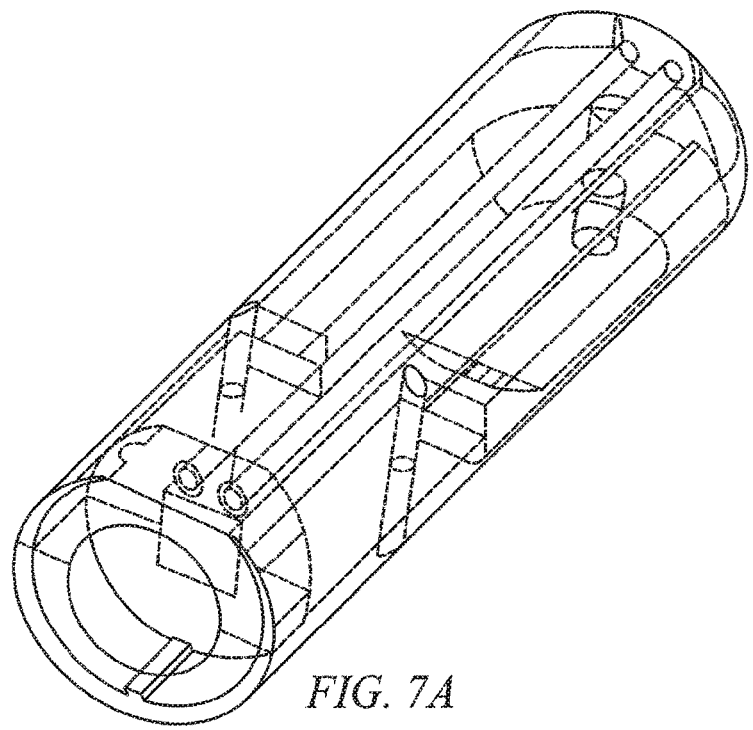
FIG. 7A is a perspective view of the cutting head from the trailing end.
Figure 7B:
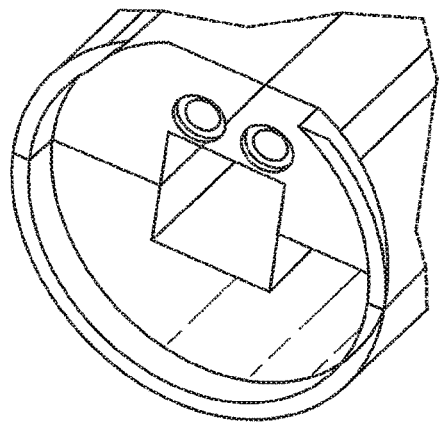
FIG. 7B is a perspective view of the cutting head from the leading end.

Cutting head 10 is depicted from its trailing and leading ends in FIGS. 7A and 7B, respectively. The hollow cylindrical space at the trailing end of said cutting head in FIG. 7A is occupied by locking mechanism 16. Face pin bores 30 receive the trailing ends of face pin depression pins 14 that urge face pin 18 into its retracted position when cutting head 10 is docked with holster 12. Face pin depression pins 14 enter into bores 30a (FIG. 7B) at the leading end of cutting head 10.

Figure 7C:
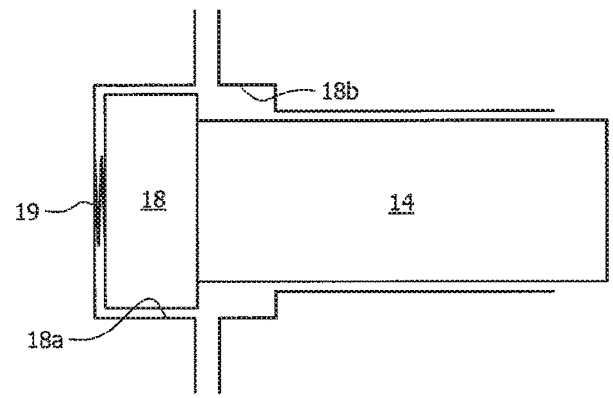
FIG. 7C is a schematic diagram of the face pin in its retracted configuration.
Figure 7D:
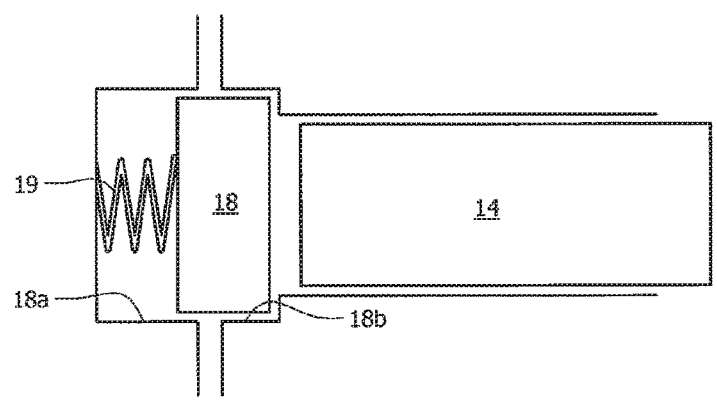
FIG. 7D is a schematic diagram of the face pin in its extended configuration.

FIG. 7C depicts the retracted position of face pin 18 and FIG. 7D depicts the extended position of said face pin. Bias means 19 in the form of a compression spring is compressed when cutting head 10 is docked in holster 12 as depicted in FIG. 7A and said spring unloads and extends face pin 18 from face pin bore 18a when cutting head 10 is disconnected from said holster 12. When so extended, face pin 18 enters into bore 18b (FIG. 7C) formed in the trailing end of cutter head 10. Bore 18b is an enlargement of the bore or bores that extends between openings 30 and 30a. As depicted in FIG. 7D, the extended position of face pin 18 prevents relative rotation between inner ring 20 and cutting head 10 because the trailing end of face pin 18 is positioned within bore 18a formed in the leading side of inner ring 20 and the leading end of face pin 18 is positioned within bore 18b formed in the trailing end of cutting head 10.

Figure 8A:
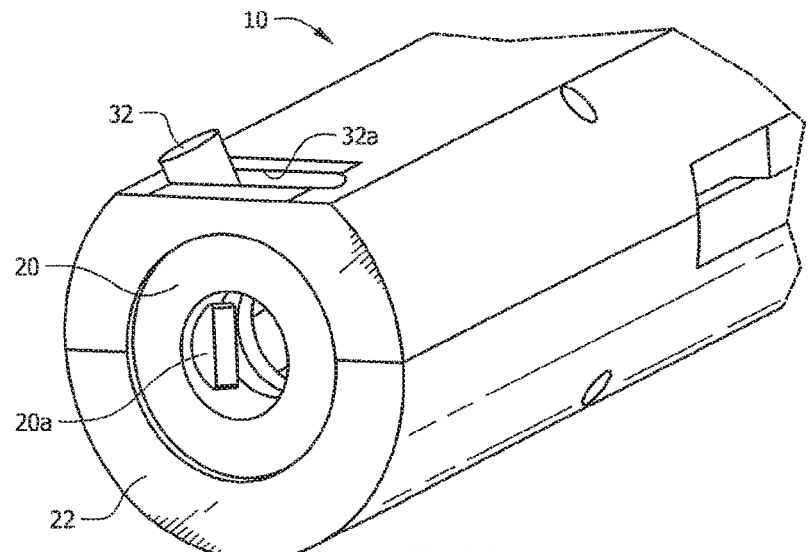
FIG. 8A is a perspective view of the trailing end of the cutting head.
Figure 8B:
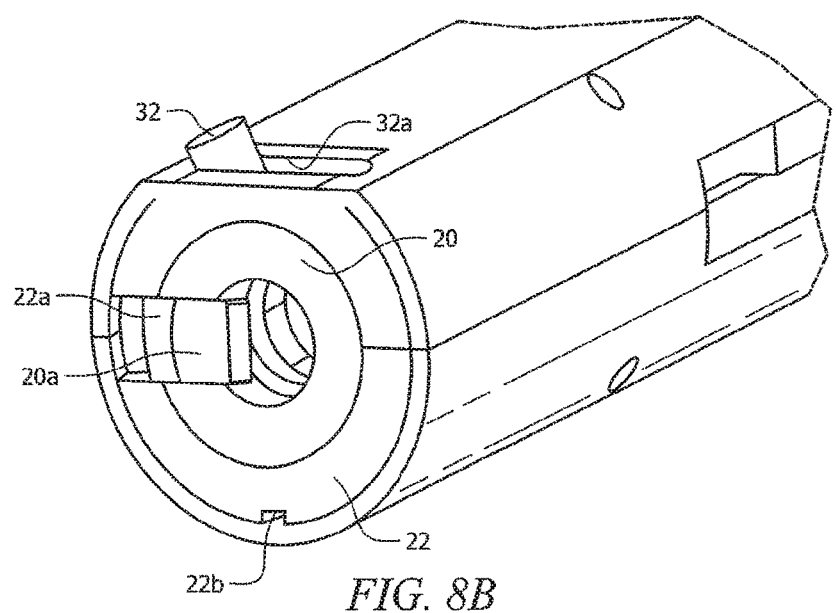
FIG. 8B is a partially cut-away view of the cutting head of FIG. 8A.
Figure 8C:
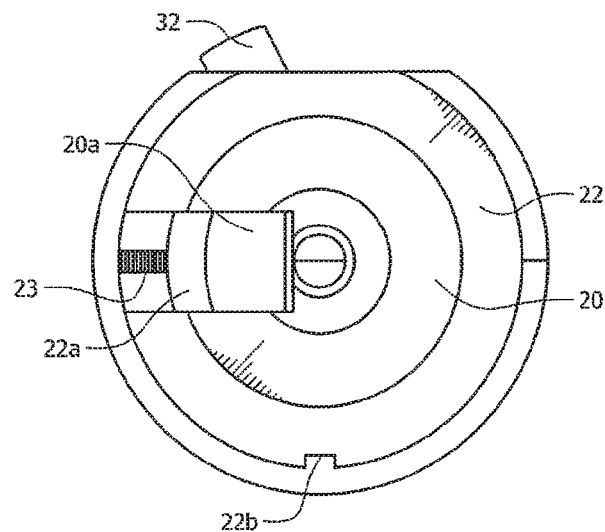
FIG. 8C is an end elevational view of the structure depicted in FIG. 8B.

FIG. 8A is a perspective view of the trailing end of cutting head 10, it being understood that cutting members 11 are positioned at the leading end thereof. FIG. 8B is a partially cut-away view of the cutting head of FIG. 8A, depicting the inner and outer locking pins 20a, 22a, respectively, in radial alignment with one another and in their respective radially innermost and locked positions. FIG. 8C is an end elevational view of the structure depicted in FIG. 8B, depicting spring 23 that urges said inner and outer lock pins in a radially inward direction when they are in alignment with one another.

Figure 9A:
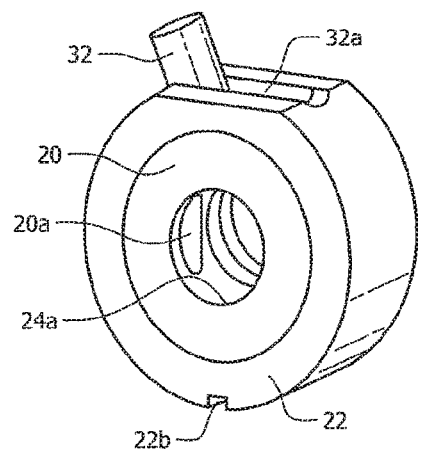
FIG. 9A is a perspective view of the novel locking means in its position of repose.
Figure 9B:
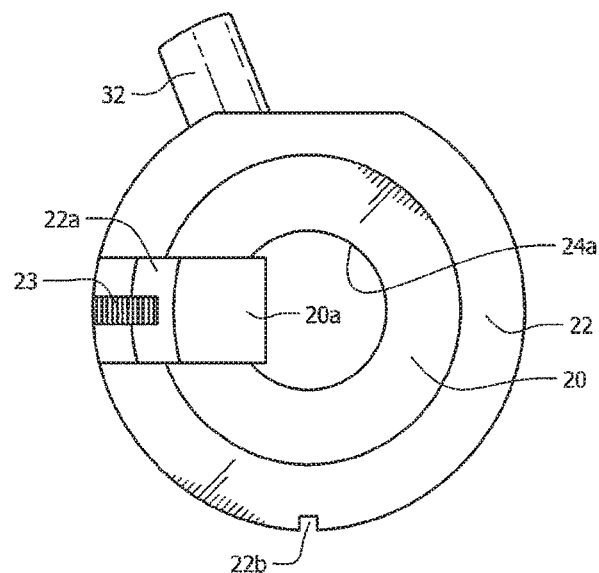
FIG. 9B is an end view of the novel locking means in its position of repose.

FIGS. 9A and 9B depict the novel locking means in its position of repose in perspective view and end view, respectively. The locking means is locked in holster 12 but outer shaft 24 is not inserted thereinto. This is position No. 1: The rotation of inner ring 20 is prevented by outer lock pin 22a. Outer lock pin 22a is urged radially inwardly by lock pin spring 23 into inner lock pin 20 which is urged radially inwardly into shaft opening 24a.

Figure 9C:
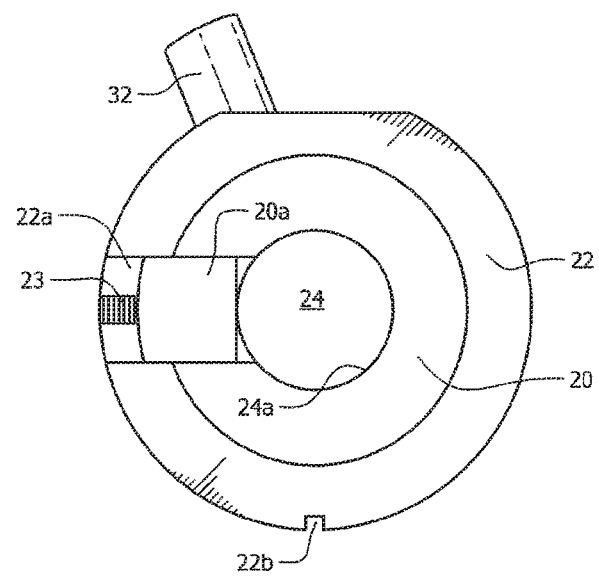
FIG. 9C depict the second position of the novel locking means.

FIG. 9C depicts the second position. As outer shaft 24 is inserted into opening 24a, said outer shaft pushes radially outwardly against inner lock pin 20a which presses radially outwardly against outer lock pin 22a, compressing lock pin spring 23. Rotation of inner lock ring 20 is prevented by inner lock pin 20a. As outer shaft 24 is inserted it pushes both lock pins 20a, 22a from their respective FIG. 9A positions, past the position in which they align with the inner and outer lock rings 20 and 22, and into position 2.

Figure 9D:
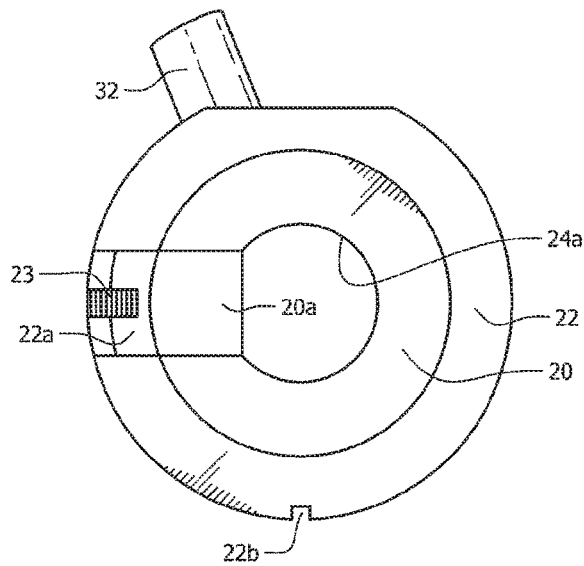
FIG. 9D depicts the third position of the novel locking means.

Position three is depicted in FIG. 9D. When outer shaft 24 is inserted to a sufficient extent, lock pin spring 23 urges inner lock pin 20a into square groove 24b of outer shaft 24. The depth of lock groove 24b is predetermined so that it allows lock pins 20a, 22a to align with lock rings 20, 22, respectively, thereby allowing inner lock ring 20 to rotate within outer lock ring 22.

Figure 9E:
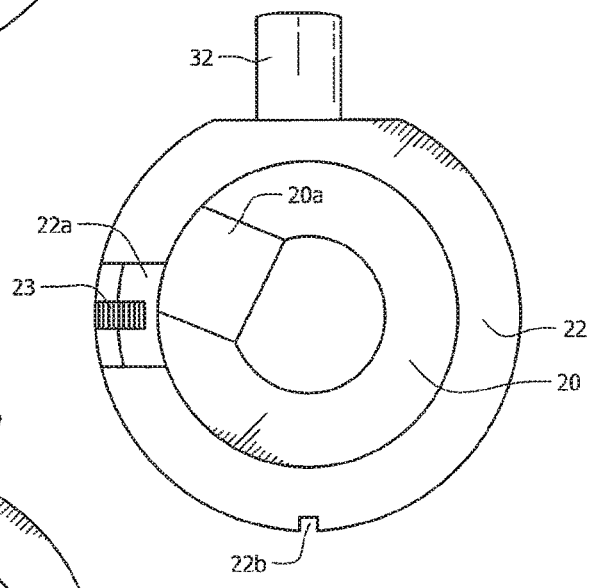
FIG. 9E depicts the novel locking means in its fourth position.

FIG. 9E depicts the fourth position. Turning outer shaft 24 clockwise allows inner lock ring 20 to rotate within outer lock ring 22. Lock pins 20a, 22a are misaligned relative to one another when inner ring 20 is rotated and inner lock pin 20a cannot be pushed radially outwardly into the outer lock pin slot. Inner lock pin 20a is secured against the inner wall or lumen of outer lock ring 22 and shaft groove 24b and cannot move (except by rotating conjointly with inner lock ring 20) until it is again aligned with outer lock pin 22a.

Figure 9F:
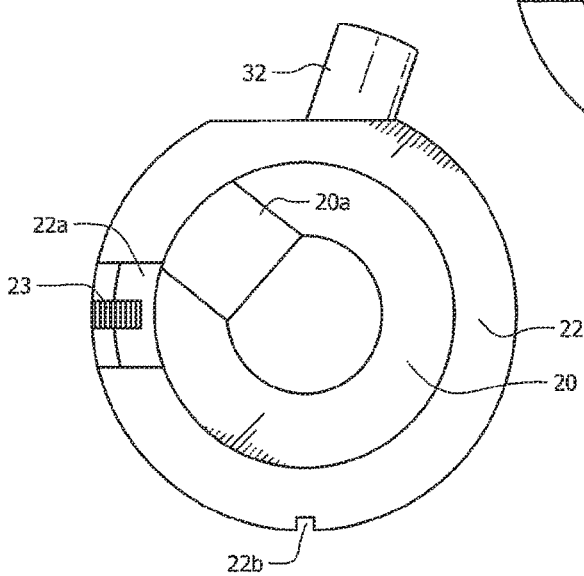
FIG. 9F depicts the novel locking means in its fifth, locked position.

FIG. 9F depicts the fifth position. This is the locked position. In this position holster lock knob 32 is captured within holster lock knob slot 12a (FIGS. 1 and 4) and cutting head 10 can be removed from holster 12. Holster lock knob 32 extends radially from inner ring 20 and rotates conjointly therewith.

When cutting head 10 is docked in holster 12, face pin 18 (FIG. 3B) is retracted into face pin bore 18a formed in the leading side of inner ring 20 by at least one face pin depression pin 14 as depicted in FIG. 7C.

Figure 10:
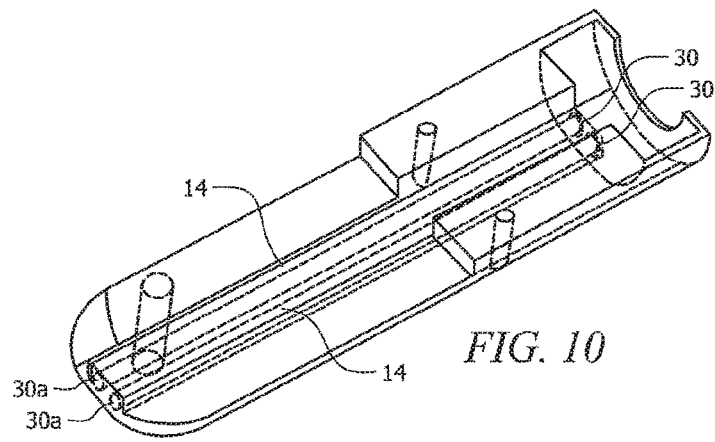
FIG. 10 is a perspective, cut-away view of the top half novel cutting head housing.

The bore or bores that receive the face pin depression pin or pins are formed in the top half of the cutting head housing as depicted in FIGS. 7A, 7B, and 10. The trailing end of the bores is denoted 30 in FIGS. 7A, 11 and 12. The leading end of said bores is denoted 30a in FIGS. 7B, 10, and 12.

Inner lock pin 20a is securely held in between the inner wall or lumen of outer lock ring 22 and outer shaft groove 24b, which also prevents outer shaft 24 from being displaced axially in or out of cutting head 10. Inner lock ring 20 is locked into place by face pin 18, and outer shaft 24 is locked into place by inner lock pin 20a.

FIG. 10 is a perspective, cut-away view of the top half novel cutting head housing.

Figure 11:
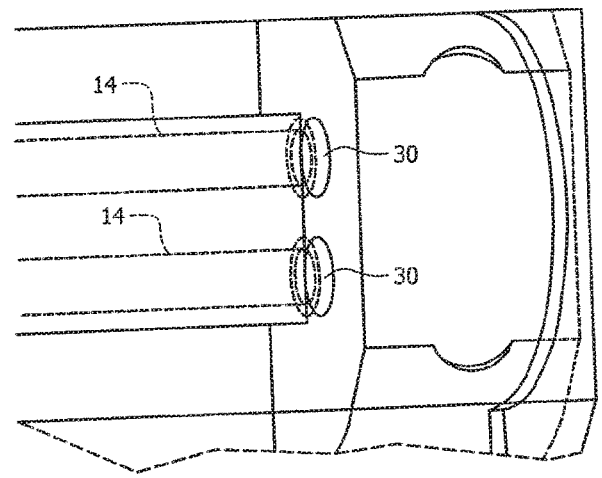
FIG. 11 is a top plan view of said top half of said cutting head housing.

FIG. 11 is a top plan view of said top half of said cutting head housing.

Figure 12:
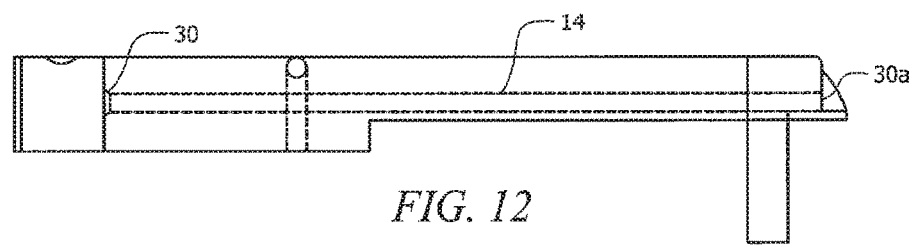
FIG. 12 is a side elevational view of said top half of said cutting head housing.
Figure 13A:
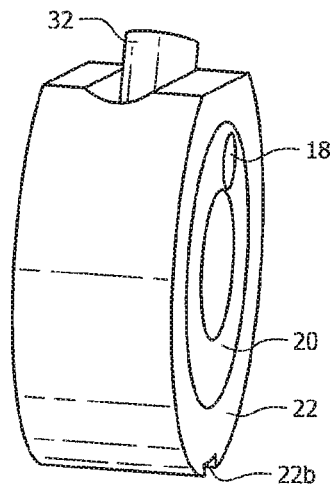
FIG. 13A is a perspective view of the novel locking means in positions one, two and three.
Figure 13B:
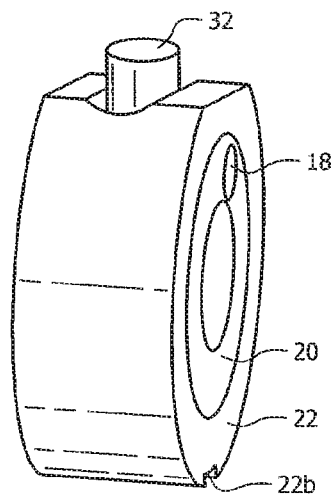
FIG. 13B is a perspective view of the novel locking means in position four.
Figure 13C:
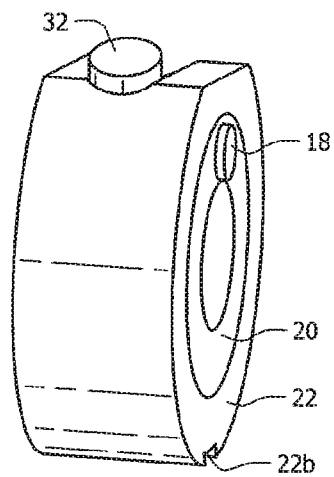
FIG. 13C is a perspective view of the novel locking means in position five.
Figure 14A:
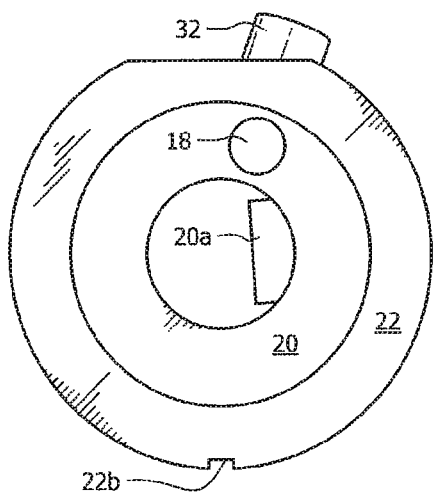
FIG. 14A is an end view of the novel locking means in position one.
Figure 14B:
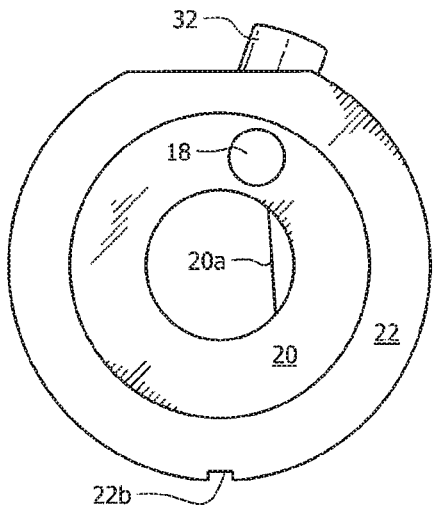
FIG. 14B is an end view of the novel locking means in position three.
Figure 14C:
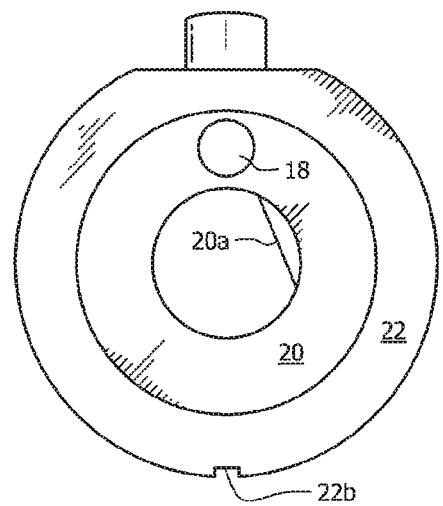
FIG. 14C is an end view of the novel locking means in position four.
Figure 14D:
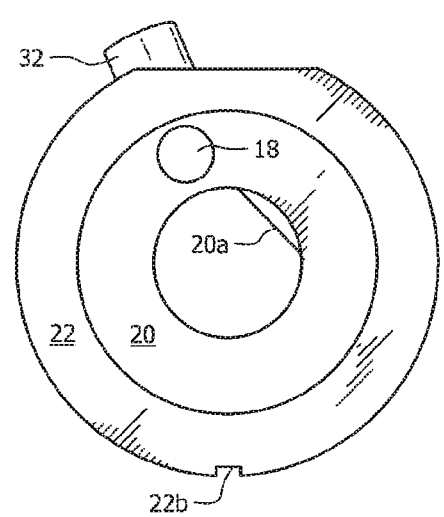
FIG. 14D is an end view of the novel locking means in position five.

FIG. 12 is a side elevational view of said top half of said cutting head housing.

The embodiments disclosed herein provide a non-invasive surgical tool that is purely mechanical in nature.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

The following claims are intended to cover all of the generic and specific features of the invention herein disclosed, and all statements of the scope of the invention which, as a matter of language, might be said to fall therebetween.

What is claimed is:
1. An incision-less laparoscopic instrument, comprising:
a holster configured for insertion into a patient's body through an umbilical port;
a cutting head removably housed within the holster, the cutting head having an operating end and a trailing end;
a first locking mechanism transitionable between a first locked configuration in which the cutting head is secured within the holster and a second unlocked configuration in which the cutting head is removable from the holster;
a shaft having a beveled leading end configured to penetrate through patient's skin and tissue, the beveled leading end of the shaft configured to engage the trailing end of the cutting head;
a second locking mechanism configured to releasably secure the beveled leading end of the shaft to the trailing end of the cutting head; and
wherein both the first and the second locking mechanisms are controlled by manipulation of the shaft.

2. The laparoscopic instrument of claim 1, wherein the first locking mechanism is controlled by rotation of the shaft about a longitudinal axis thereof, and the second locking mechanism is controlled by translation of the shaft along the longitudinal axis thereof.

3. The laparoscopic instrument of claim 1, the first locking mechanism comprising:
an elongated circumferential groove disposed on the holster;
a lock pin radially protruding from the trailing end of the cutting head, the lock pin residing within the elongated circumferential groove when the first locking mechanism is in the first locked configuration;

whereby axial rotation of the shaft causes the lock pin to exit the elongated circumferential groove thereby transitioning the first locking mechanism into the second unlocked configuration thus releasing the cutting head from the holster.

4. The laparoscopic instrument of claim 1, the second locking mechanism comprising:
   an annular lock ring rotationally disposed with the trailing end of the cutting head, the annular lock ring configured to receive the beveled leading end of the shaft;
   a pin retractably disposed with respect to the annular lock ring;
   a groove disposed on the beveled leading end of the shaft, the elongated circumferential groove configured to receive the pin, whereby the pin immobilizes the shaft with respect to the annular lock ring.

5. The laparoscopic instrument of claim 4, wherein the pin further immobilizes the annular lock ring against rotation relative to the cutting head, whereby insertion of the beveled leading end of the shaft into the annular lock ring displaces the pin thereby enabling the annular lock ring to rotate relative to the cutting head.

6. The laparoscopic instrument of claim 1, further comprising a third locking mechanism configured to selectively immobilize the shaft against axial rotation relative to the cutting head.

7. The laparoscopic instrument of claim 6, the third locking mechanism comprising:
   an annular lock ring rotationally disposed within the trailing end of the cutting head, the annular lock ring having a face;
   a face pin retractably disposed within the annular lock ring, the face pin having a retracted position in which the face pin is flush with the face of the annular lock ring and an extended position in which the face pin protrudes beyond the face of the annular lock ring;
   a bore disposed in the trailing end of the cutting head, the bore configured to receive the face pin when the face pin is in the extended position;
   whereby the face pin prevents relative rotation between the annular lock ring and the cutting head when the face pin is within the bore.

8. The laparoscopic instrument of claim 1, the first locking mechanism comprising:
   an annular lock ring rotationally disposed within the trailing end of the cutting head, the annular lock ring having a face;
   a face pin retractably disposed within the annular lock ring, the face pin having a retracted position in which the face pin does not protrude beyond the face of the annular lock ring and an extended position in which the face pin protrudes beyond the face of the annular lock ring;
   a first bore disposed within the cutting head, wherein the face pin resides within the first bore when the cutting head is undocked from the holster thereby immobilizing the annular lock ring against rotation relative to the cutting head;
   a first depression pin disposed within the holster, the first depression pin configured to push the face pin out of the first bore, thereby enabling the annular lock ring to rotate relative to the cutting head thus enabling docking of the cutting head within the holster.

9. The laparoscopic instrument of claim 8, further comprising:
   a second bore disposed within the cutting head;
   a second depression pin disposed with the holster;
   wherein the second depression pin is configured to push the face pin out of the second bore, thereby enabling the annular lock ring to rotate relative to the cutting head to a position in which the face pin enters the first bore, whereby the face pin remains within the first bore while the cutting head is undocked.

10. The laparoscopic instrument of claim 1 further comprising an inner shaft disposed within an inner lumen of the shaft, whereby axial translation of the inner shaft controls the operating end of the cutting head.

11. An incision-less laparoscopic instrument, comprising:
    a holster configured for insertion into a patient's body through an umbilical port;
    a cutting head removably housed within the holster, the cutting head having an operating end and a trailing end;
    an annular lock ring rotationally disposed within the trailing end of the cutting head, wherein rotation of the annular lock ring relative to the cutting head locks and unlocks the cutting head relative to the holster;
    a shaft having a beveled leading end configured to penetrate through patient's skin and tissue, the beveled leading end of the shaft configured to couple to the annular lock ring;
    a locking mechanism restricting rotation of the annular lock ring relative to the cutting head; and
    wherein the locking mechanism is controlled by manipulation of the shaft.

12. The laparoscopic instrument of claim 11, further comprising:
    an elongated circumferential groove disposed on the holster;
    a lock pin radially disposed on the annular lock ring, the lock pin protruding from the cutting head, wherein the lock pin resides within the elongated circumferential groove thus securing the cutting head within the holster;
    whereby axial rotation of the shaft causes the lock pin to exit the elongated circumferential groove thereby releasing the cutting head from the holster.

13. The laparoscopic instrument of claim 11, further comprising:
    a pin retractably disposed relative to the annular lock ring;
    a groove disposed on the beveled leading end of the shaft, the elongated circumferential groove configured to receive the pin, whereby the pin secures the shaft within the annular lock ring.

14. The laparoscopic instrument of claim 13, wherein the pin further immobilizes the annular lock ring against rotation relative to the cutting head, whereby insertion of the beveled leading end of the shaft into the annular lock ring displaces the pin thereby enabling the annular ring to rotate relative to the cutting head.

15. The laparoscopic instrument of claim 11, the locking mechanism comprising:
    a face pin retractably disposed within the annular lock ring, the face pin having a retracted position in which the face pin is flush with a face of the annular lock ring and an extended position in which the face pin protrudes beyond the face of the annular lock ring;
    a bore disposed within the trailing end of the cutting head, the bore configured to receive the face pin when the face pin is in the extended position;
    whereby the face pin prevents relative rotation between the annular lock ring and the cutting head when the face pin is within the bore.

16. The laparoscopic instrument of claim 11, the locking mechanism comprising:
- a face pin retractably disposed within the annular lock ring, the face pin having a retracted position in which the face pin does not protrude beyond a face of the annular lock ring and an extended position in which the face pin protrudes beyond the face of the annular lock ring;
- a first bore disposed within the cutting head, wherein the face pin resides within the first bore when the cutting head is undocked from the holster thereby immobilizing the annular lock ring against rotation relative to the cutting head;
- a first depression pin disposed within the holster, wherein the first depression pin configured to push the face pin out of the first bore, thereby enabling the annular lock ring to rotate relative to the cutting head thus enabling docking of the cutting head within the holster.

17. The laparoscopic instrument of claim 16, further comprising:
- a second bore disposed within the cutting head;
- a second depression pin disposed with the holster;
- wherein the second depression pin is configured to push the face pin out of the second bore, thereby enabling the annular lock ring to rotate relative to the cutting head to a position in which the face pin enters the first bore, whereby the face pin remains within the first bore while the cutting head is operational.

* * * * *